US006824998B2

(12) United States Patent
Davidson et al.

(10) Patent No.: US 6,824,998 B2
(45) Date of Patent: Nov. 30, 2004

(54) COMPOUNDS AND METHODS FOR DETECTING TRIPEPTIDYL PROTEASE I

(75) Inventors: Beverly L. Davidson, North Liberty, IA (US); David Wiemer, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 10/393,438

(22) Filed: Mar. 19, 2003

(65) Prior Publication Data

US 2004/0185520 A1 Sep. 23, 2004

(51) Int. Cl.[7] .......................... G01N 33/53; C12Q 1/37; C12N 9/48; C07K 5/00
(52) U.S. Cl. .................. 435/7.72; 435/24; 435/212; 530/331
(58) Field of Search .................. 435/7.72, 24, 212; 530/331; 513/331

(56) References Cited

PUBLICATIONS

"Webster's II New Riverside University Dictionary", 1984 (Houghton Mifflin: boston) p. 667.*
Streitwieser et al. "Introduction to Organic Chemistry" 1981 (Macmillan Publishing New York) pp. 388–389.*
Flockenhaus et al. "The occurrence of a Tripeptidyl Peptidase I in Trophozoites of Entamoeba histolytica" Arch. Med. Res. (2000) 31(4, Suppl.) pp. S67–S68.*
Kim, M.K. et al., "Tripeptide Probes for Tripeptidyl Protease I Production via Gene Transfer," J. Med. Chem., 2003, pp. 1603–1608.
Kim, M.K. et al., "EDC–Mediated Condensations of 1–Chloro–5–Hydrazino–9, 10–anthracenedione, 1–hydrazino–9, 10–anthracenedione, and the corresponding anthrapyrazoles," Tetrahedron Letters, 45, 2004, pp. 4977–4980.

Bernardini et al., "The Substrate Range of Tripeptidyl–Peptidase I", European Journal of Paediatric Neurology, 5, 69–72 (2001).
Dikov et al., "Original Method for the Histochemical Demonstration of Tripeptidyl Aminopeptidase I", Cellular and Molecular Biology, 46, 1219–1225 (2000).
Du et al., "Rat Tripeptidyl Peptidase I: Molecular Cloning, Functional Expression, Tissue Localization and Enzymatic Characterization", Biol. Chem., 382, 1715–1725 (2001).
Haskell et al., "Viral–Mediated Delivery of the Late–Infantile Neuronal Ceroid Lipofuscinosis Gene, TPP–I to the Mouse Central Nervous System", Gene Therapy, 10, 34–42 (2003).
Kida et al., "Distribution of Tripeptidyl Peptidase I in Human Tissues Under Normal and Pathological Conditions", Journal of Neuropathology and Experimental Neurology, 60, 280–292 (2001).
Kim et al., "Tripeptide Probes for Tripeptidyl Protease I Production via Gene Transfer", J. Med. Chem., 46, 1603–1608 (2003).
Lin et al., "Production and Characterization of Recombinant Human CLN2 Protein for Enzyme–Replacement Therapy in Late Infantile Neuronal Ceroid Lipofuscinosis", Biochem. J., 357, 49–55 (2001).

* cited by examiner

Primary Examiner—Jean C. Witz
Assistant Examiner—Susan Hanley
(74) Attorney, Agent, or Firm—Fish & Richardson P.C., P.A.

(57) ABSTRACT

The present invention provides compounds useful for the detection of the enzyme tripeptidyl protease I (TPP-1). The invention also provides methods of making such compounds, methods of using such compounds, and kits and compositions containing such compounds. In one embodiment, Gly-L-Pro-L-Ser-1-anthraquinonylhydrazide, in combination with p-anisaldehyde, is used to detect TPP-1.

18 Claims, 1 Drawing Sheet

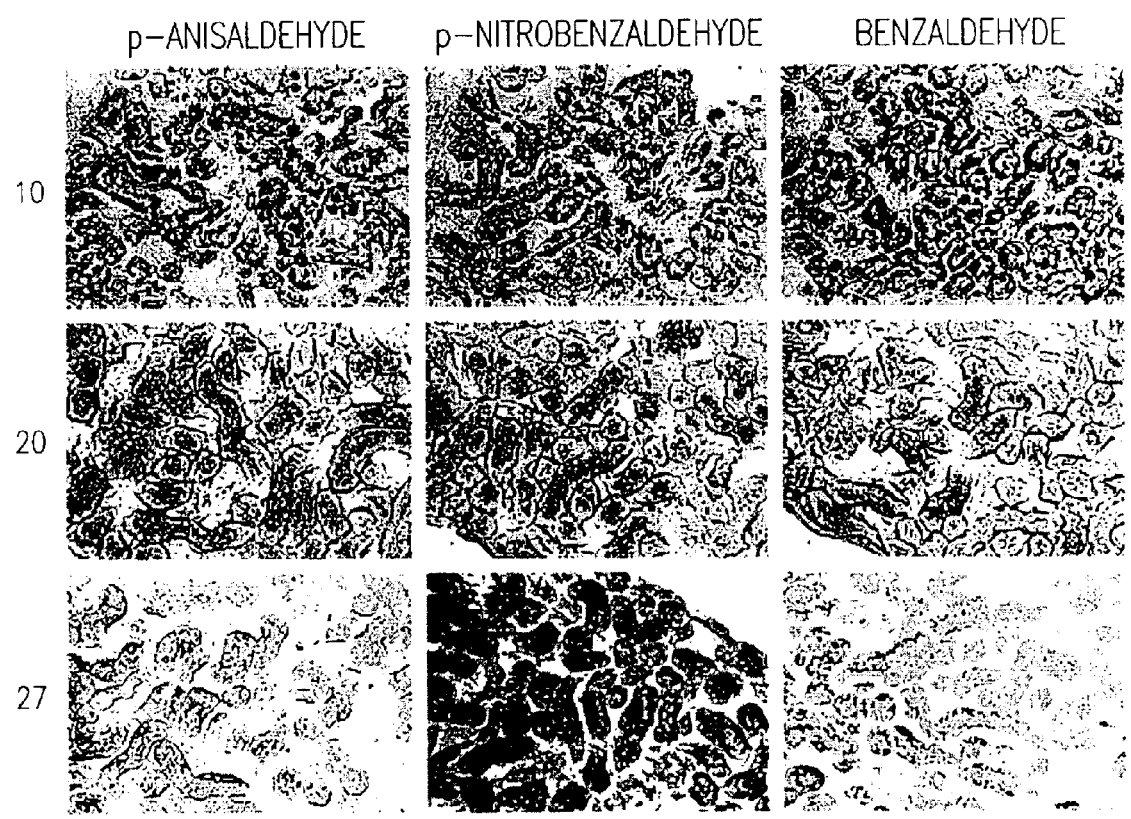

COMPOUNDS AND METHODS FOR DETECTING TRIPEPTIDYL PROTEASE I

FIELD OF THE INVENTION

The present invention provides compounds useful for the detection of the enzyme tripeptidyl protease I (TPP-1). The invention also provides methods of making such compounds, methods of using such compounds, and kits and compositions containing such compounds. In one embodiment, Gly-L-Pro-L-Ser-1-anthraquinonylhydrazide, in combination with p-anisaldehyde, is used to detect TPP-1.

BACKGROUND OF THE INVENTION

Mutations in the CNL2 gene result in neuronal ceroid lipofuscinoses (NCL's), a group of rare but devastating neurodegenerative diseases (Bennett et al., 1999). One type of NCL, known as classical late-infantile neuronal ceroid lipofuscinosis (LINCL), Jansky-Bielschowsky disease, CLN2 deficiency, or pepinase deficiency, presents as an acute seizure disorder at about 4–6 years of age, and includes rapid loss of visual, motor, and cognitive functions (Mole, 1998). Recent studies have shown that this disease is characterized by a deficiency in the soluble lysosomal protease tripeptidyl protease I (TPP-1; also known as tripeptidyl peptidase I or tripeptidyl aminopeptiase I) (Sleat et al., 1997), and that inactivating mutations of TPP-1 result in accumulation of storage material in the lysosome (Palmer, 1995). TPP-1 is a non-membrane bound lysosomal enzyme that can be secreted from cells over-expressing the enzyme, and taken up by deficient cells (Haskell et al., 2003). Thus, partial enzyme replacement will likely ameliorate the storage deficit.

Despite the increased understanding of the basis of this disease, current therapy for LINCL can only relieve the seizure disorder and cannot address the underlying cause or the progression of the disease (Bennett et al., 1999, Sleat et al., 1997). Furthermore, a major limitation in the development of gene-based therapies for neurodegenerative diseases, and more specifically TPP-1 deficiency, is assays to assess the distribution of the enzyme.

Thus, there is currently a need for additional substrates and methods useful for detecting TPP-1. For example, there is a need for additional substrates and methods that can provide specific information on TPP-1 distribution following enzyme replacement or gene transfer therapy.

SUMMARY OF THE INVENTION

Tripeptide derivatives of anthraquinones have been prepared and tested as histochemical reagents for detection of TPP-1. One compound, derived from 5-chloroanthraquinone hydrazide, was identified as a tetracyclic pyrazoanthrane based on analysis of $^{13}C$ NMR data, while four others were tripeptide derivatives of the tricyclic anthraquinone hydrazide. The compound Gly-L-Pro-L-Ser anthraquinone hydrazide was the most effective histochemical reagent for detecting TPP-1, particularly when combined with p-anisaldehyde.

Thus, the present invention provides a compound of formula I:

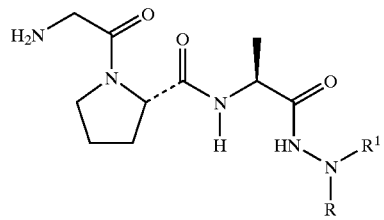

or a salt thereof, wherein
R is an anthraquinone, and
$R^1$ is
(a) H, or
(b) $C_{1-6}$alkyl.

A compound of formula I is Gly-L-Pro-L-Ala-1-anthraquinonylhydrazide, or a salt thereof.

The present invention also provides a compound of formula II:

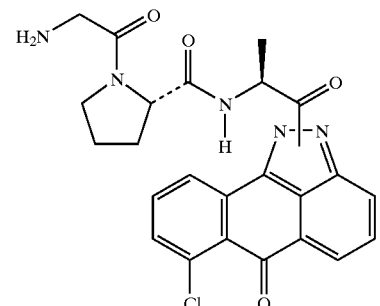

or a salt thereof.

A compound of formula II is Gly-L-Pro-L-Ala-5-chloro-1-anthra[1,9-cd]pyrozol-6(2H)-one, or a salt thereof.

The present invention further provides a compound of formula III:

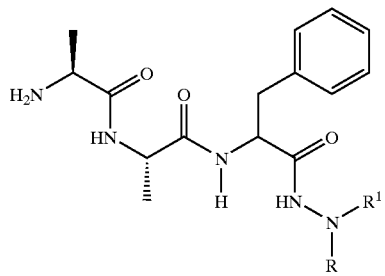

or a salt thereof, wherein
R is an anthraquinone, and
$R^1$ is
(a) H, or
(b) $C_{1-6}$alkyl.

A compound of formula III is L-Ala-L-Ala-L-Phe-1-anthraquinonylhydrazide, or a salt thereof.

The invention also provides compositions including compounds of the invention useful for detecting or determining TPP-1.

The invention further provides a method for detecting or determining TPP-i in a biological sample obtained from a mammal. In some embodiments, TPP-1 can be detected or determined following enzyme replacement or gene transfer therapy, for example, following virally-mediated gene transfer of a construct encoding TPP-1.

The invention also includes kits for carrying out the methods of the invention.

The invention also provides novel compounds, e.g., intermediates, and methods that are useful in preparing compounds of formula I, II or III.

BRIEF DESCRIPTION OF THE FIGURES

FIG. 1. Compounds 10, 20, and 27 were compared for sensitivity for detecting TPP-1 activity on frozen sections of murine kidney tissue using conditions to control the rate of crystalline formation and diffusion of product. Compounds 10, 20, and 27 were readily hydrolyzed by endogenous TPP-1 in murine tissues, revealing lysosomal accumulation of precipitates. The aldehydes p-NBA and p-AA were more effective than benzaldehyde itself with regard to precipitate density and color. The combination of tripeptide 20 and p-AA was most sensitive, resulting in purple precipitates in areas of high endogenous enzyme activity.

DETAILED DESCRIPTION OF THE INVENTION

The present invention provides compounds, methods, and kits useful for detecting or determining tripeptidyl protease I (TPP-1). TPP-1 hydrolyzes tripeptides from the N-terminal of polypeptides. By synthesizing compounds that include appropriate hydrolysable peptides, and linking those peptides to groups that are able to be detected following hydrolysis by TPP-1, it is possible to synthesize compounds that are useful to detect TPP-1.

In some embodiments, the compounds of the invention include tripeptides composed of three amino acids. In some embodiments, the tripeptides are Gly-Pro-Ser, Gly-Pro-Ala, or Ala-Ala-Phe. In some embodiments, the tripeptide is Phe-Phe-Phe. In some embodiments of the invention, the compounds include peptides that are longer than 3 amino acids in length. In some embodiments, the compounds include peptides that are 4, 5, 6, 7, 8, 9, or 10 amino acids in length.

"Amino acid," includes a residue of natural amino acid (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). An amino acid can conveniently be linked to the remainder of a compound through, for example, its carboxy terminus.

The compounds of the invention include a detectable group that is able to be detected following hydrolysis by TPP-1. In some embodiments, the detectable group that is able to be observed is an anthraquinone, for example, an anthraquinone hydrazide. In some embodiments, the compounds include a group with an aromatic ring system and a hydrazine group, for example, the detectable group may be an aromatic hydrazine.

The invention also provides compositions including compounds of the invention useful for detecting or determining TPP-1. In some embodiments, the composition contains the compounds of the invention at a concentration of about 1 mM. The composition may also contain a buffer, for example, an acetate buffer. In some embodiments, the acetate buffer is 0.1 M acetate buffer. The compositions can also optionally include an aromatic aldehyde. In some embodiments, the compositions include p-anisaldehyde, p-nitrobenzaldehyde, or benzaldehyde. In some embodiments, the p-anisaldehyde, p-nitrobenzaldehyde, or benzaldehyde are present in the composition at a concentration of about 1 mg/ml. In some embodiments of the invention, methyl substituted benzaldehydes are included. In some embodiments of the invention, ethyl or alkyl substituted benzaldehydes are included. Ortho and meta isomers of these compounds may also be included in some embodiments of the invention.

The invention further provides a method for detecting or determining TPP-1 in a biological sample, e.g., a physiological sample obtained from a mammal, e.g., a mouse or a human, including contacting the sample with a composition of the invention and detecting or determining TPP-1 in the sample. In some embodiments, the biological sample may be a tissue sample, e.g., a biopsy sample. In some embodiments of the invention, the tissue sample is from the central nervous system, for example, the brain. In some embodiments, the sample may be a fluid sample, e.g., cerebrospinal fluid.

TPP-1 can be detected or determined following enzyme replacement or gene transfer therapy, for example, following gene transfer to a mammal of a construct encoding TPP-1. Such a gene transfer method is described in Haskell et al. (2003), the disclosure of which is incorporated by reference. In some circumstances, TPP-1 is detected or determined prior to enzyme replacement or gene transfer therapy, and then detected or determined at least at one time point after enzyme replacement or gene transfer therapy, and the results are compared to evaluate the effectiveness of the enzyme replacement or gene transfer therapy. When TPP-1 is detected or determined at multiple time points, the samples used at the different time points are in some embodiments from the same subject and in some embodiments from different subjects. A method for detecting TPP-1 in a tissue sample is provided herein in Example 2.

The invention also includes kits for carrying out the methods of the invention. Such kits include, in one or more containers, usually conveniently packaged to facilitate use in assays, quantities of various compositions for carrying out the methods of the invention. The kit may also include instructions on its use. For example, the present invention provides a kit, including a compound of the invention and a first container, packaging material, and instructions for the use of the kit to detect or determine tripeptidyl protease 1 in a biological sample. The compound may be disposed in the first container. In some embodiments, the kit includes p-anisaldehyde. In some embodiments, the kit includes a second container, wherein p-anisaldehyde is disposed in the second container. In some embodiments, the kit includes p-nitrobenzaldehyde. In some embodiments, the kit includes a second container, wherein p-nitrobenzaldehyde is disposed in the second container. In some embodiments, the kit includes benzaldehyde. In some embodiments, the kit includes a second container, wherein benzaldehyde is disposed in the second container.

The invention also provides novel compounds, e.g., intermediates, and methods that are useful in preparing compounds of formula I, II or III.

Salts of compounds of the invention may be obtained using standard procedures, for example, by reacting a sufficiently basic compound with a suitable acid. Alkali metal (for example, sodium, potassium or lithium) or alkaline earth metal (for example calcium) salts of carboxylic acids can also be made. In one embodiment, the compounds of the invention are bromide salts.

The carbon atom content of various hydrocarbon-containing moieties is indicated by a prefix designating a lower and upper number of carbon atoms in the moiety, i.e., the prefix $C_{i-j}$ indicates a moiety of the integer "i" to the integer "j" carbon atoms, inclusive. For example, $C_{1-6}$alkyl refers to an alkyl of one to six carbon atoms, inclusive.

"Alkyl" denotes both straight and branched groups; but reference to an individual radical such as "propyl" embraces only the straight chain radical. When alkyl can be partially unsaturated, the alkyl chain may comprise one or more (e.g., 1, 2, 3, or 4) double or triple bonds in the chain.

For example, $C_{1-7}$alkyl may be methyl, ethyl, propyl, isopropyl, butyl, iso-butyl, sec-butyl, pentyl, 3-pentyl, or hexyl.

The invention will now be described by the following non-limiting examples.

EXAMPLE 1

Synthesis of Compounds

Tripeptides derived from 5-chloroanthraquinone hydrazide and anthraquinone hydrazide were prepared as potential reagents to probe cellular expression of TPP-1.

Attempted chemical synthesis of Gly-L-Pro-L-Ala-chloroanthraquinone hydrazide, a compound reported to serve as a substrate for TPP-1 (Dikov et al., 2000; see Scheme 1 as reported in Dikov et al., 2000), was complicated by formation of a pyrazoloquinone. In contrast, formation of a pyrazoloquinone was not observed during coupling reactions with anthraquinone hydrazide. Several tripeptide derivatives of this compound were prepared.

Scheme 1

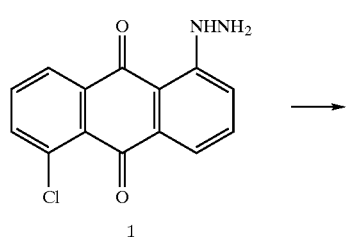

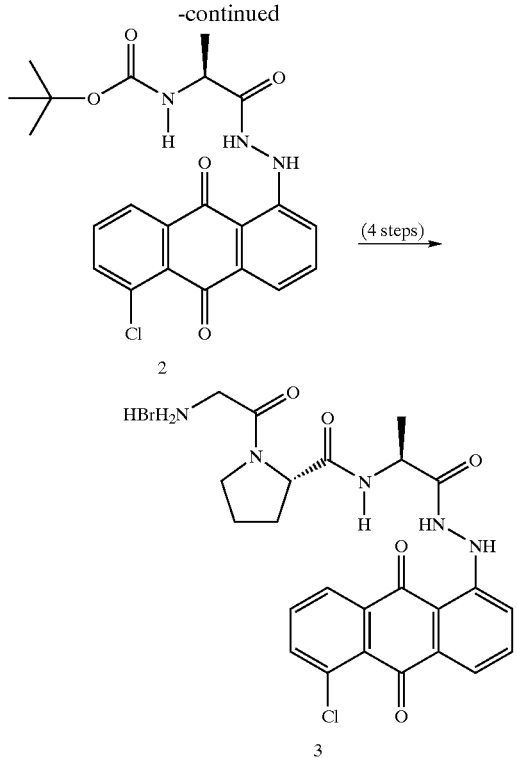

5-Chloroanthraquinone hydrazide (1) was prepared from commercial 1,5-dichloroanthraquinone (4) through reaction with hydrazine (Scheme 2) (Moehlau, 1912). Coupling of this hydrazine with tBOC-L-Ala was first conducted through reaction with DCC. However, this procedure gave a coupled product only in low yield. The same material was obtained in much better yield through a coupling mediated with the DCC substitute 1-(3-dimethylaminopropyl)-3-ethylcarbodiimide hydrochloride (EDC.HCl) (Sheehan et al., 1961; Xu et al., 1998). The product initially was assumed to be the amide 2 depicted in Scheme 1 (Dikov et al., 2000). However, analysis of the NMR data for this series of compounds did not support assignment of the structures previously proposed for the coupled products. Of special significance is the $^{13}$C NMR data. The symmetrical anthraquinone 4 shows a single resonance at 180.9 ppm that can be assigned to the quinone carbonyl carbons. In the hydrazine derivative 1 this symmetry is lost, and two quinone resonances are observed at 183.8 and 182.5 ppm. However, in the product of the DCC and EDC.HCl coupling reactions with tBOC-L-Ala, only one carbonyl resonance is apparent (181.1 ppm). Because the expected total of 16 aromatic or carbonyl resonances is observed, it is not possible that an accidental overlap of two resonances has occurred. Instead, it appears probable that cyclization to a pyrazole derivative occurred under these conditions, as previously observed with alkyl-substituted hydrazines derived from related anthraquinones (Bradley et al., 1952). Further coupling with tBOC-L-Ala might afford an N-acylated derivative such as compound 5 or its regioisomeric N-acylated product 6.

To explore the possibility of pyrazole formation, quinone 4 was treated with hydrazine for an extended period, and the pyrazole 7 (Bradley et al., 1952) was obtained. Only a single carbonyl resonance was observed in the $^{13}$C spectrum of this product.

Scheme 2

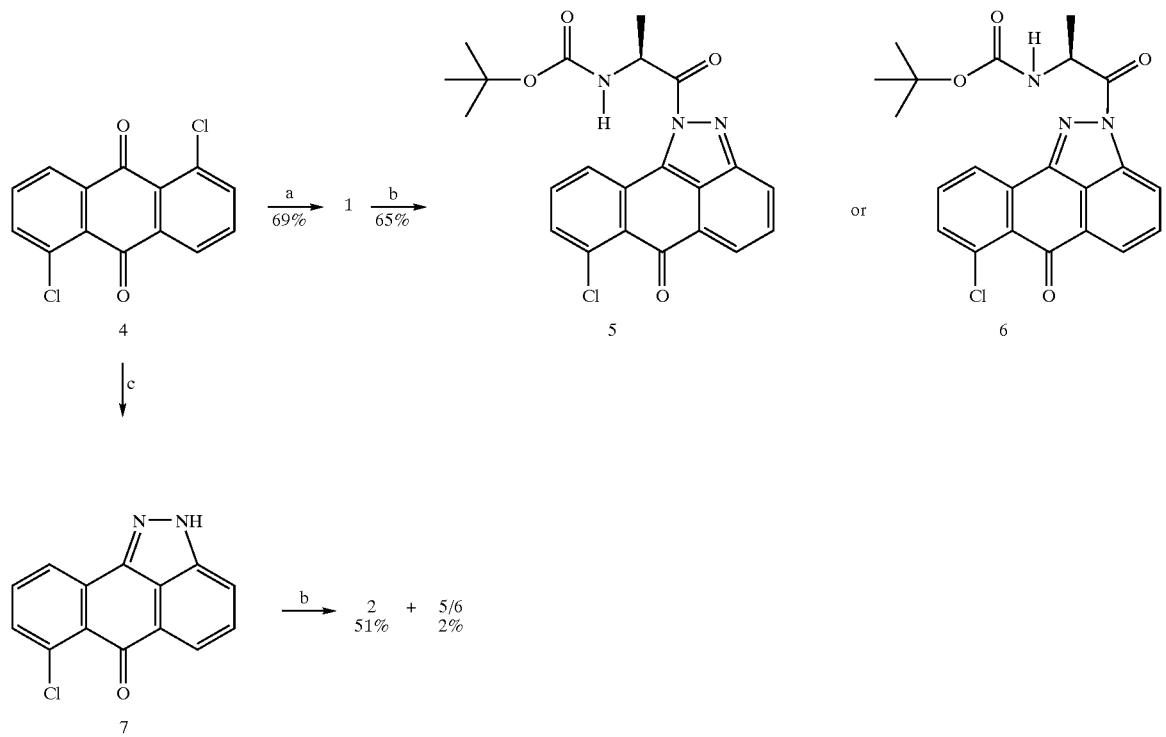

Reagents and conditions: (a) NH₂NH₂•H₂O, Pyr, reflux; (b) N-tBOC-Ala, EDC•HCl, HOBt, NMM, THF; (c) NH₂NH₂•H₂O, iPr₂NEt, THF, reflux The pyrazole derivative 5 (or 6) was carried on to the corresponding tripeptide (Scheme 3). After hydrolysis of the tBOC group gave the free amine 8, an EDC.HCl-mediated coupling with tBOC-Gly-L-Pro afforded the protected tripeptide 9 and final cleavage of the tBOC group gave the tripeptide 10 (Scheme 3).

Scheme 3

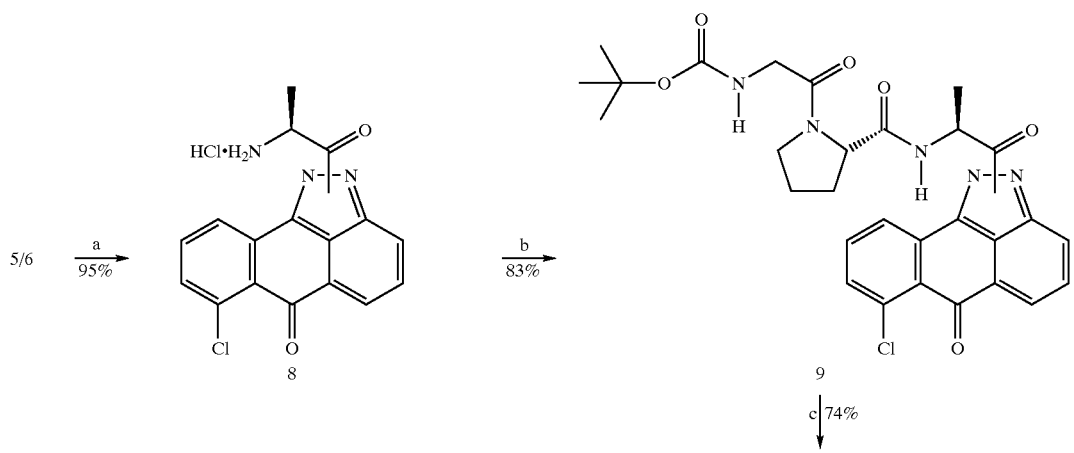

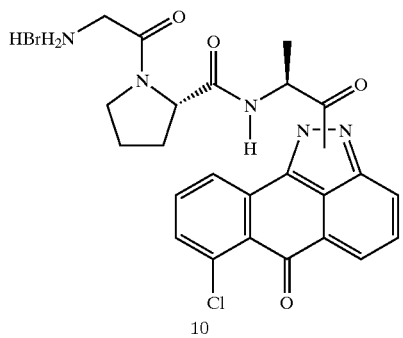

Reagents and conditions: (a) 6N•HCl/Dioxane; (b) N-tBOC-Gly-Pro, EDC•HCl, HOBt, NMM; THF; (c) 30% HBr/AcOH Additional tripeptides were derived from commercial 1-chloroanthraquinone 11 (Scheme 4). Treatment of compound 11 with hydrazine gave the expected hydrazine group to afford the amino acid 18, coupling with tBOC-Gly L-Pro to obtain the protected tripeptide 19, and final deprotection gave the tripeptide 20.

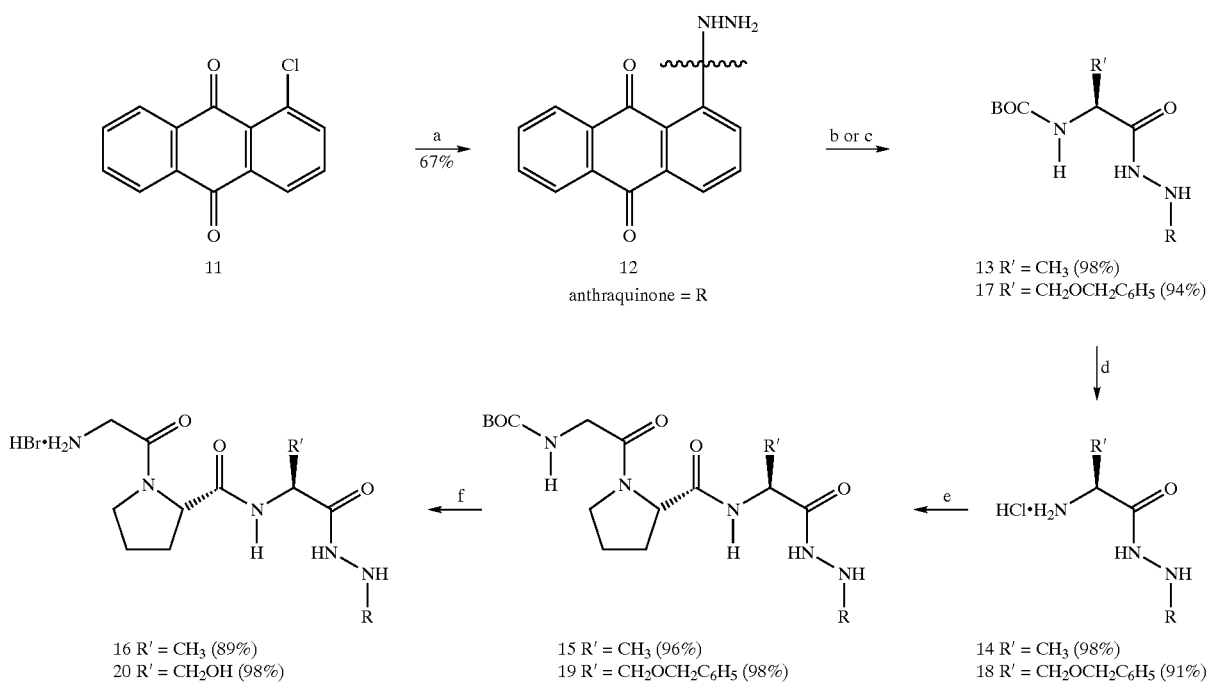

Reagents and conditions: (a) NH$_2$NH$_2$•H$_2$O, pyr, reflux; (b) N-tBOC-L-Ala, EDC•HCl, HOBt, NMM, THF;
(c) N-tBOC-O-benzyl-L-Ser, EDC•HCl, HOBt, NMM, THF; (d) 6N-HCl/dioxane; (e) N-tBOC-Gly-L-Pro, EDC•HCl, HOBt, NMM, THF; (f) 30% HBr/AcOH derivative 12 (Moehlau, 1912). Treatment of compound 12 with EDC.HCl and tBOC-L-Ala gave the protected peptide 13 rather than a pyrazole type product, as evidenced by observation of two quinone carbons at ~180 ppm. Hydrolysis of the tBOC group gave the desired amine 14 in good yield. Standard EDC.HCl coupling with tBOC-Gly-L-Pro and subsequent reaction with HBr to cleave the tBOC group gave the desired tripeptide 16. A third tripeptide was prepared through use of tBOC-O-Bz-L-Ser in the first coupling reaction to obtain the protected amino acid hydrazide 17. A parallel reaction sequence involving hydrolysis of the tBOC The hydrazine 12 was treated with tBOC-L-Phe to obtain the coupled product 21 (Scheme 5). After removal of the tBOC group gave the free amine 22, coupling with tBOC-L-Ala gave the protected dipeptide 23. In this case, deprotection was accomplished in good yield by reaction with HBr, but partial racemization occurred to give a 3:1 mixture of two diastereomers. The major diastereomer (24) was allowed to react with tBOC-L-Ala to obtain the protected tripeptide 26, and final deprotection gave the desired target compound 27. Instead of conducting a parallel sequence with the minor diastereomer 25, tBOC-D-Phe was coupled with hydrazine 12 to obtain the R isomer 28. After deprotection to the free amine 29, EDC.HCl-mediated coupling with tBOC-L-Ala-L-Ala gave the protected tripeptide 30, and final cleavage of the tBOC group gave the tripeptide derivative 31.

otherwise noted, with $(CH_3)_4Si$ ($^1H$, 0.0 ppm) or $CDCl_3$ ($^{13}C$, 77.0 ppm) as internal standards. Low-resolution electron impact (EI) mass spectra were recorded with a Hewlett-Packard 6890 instrument operating at 70 eV (only selected

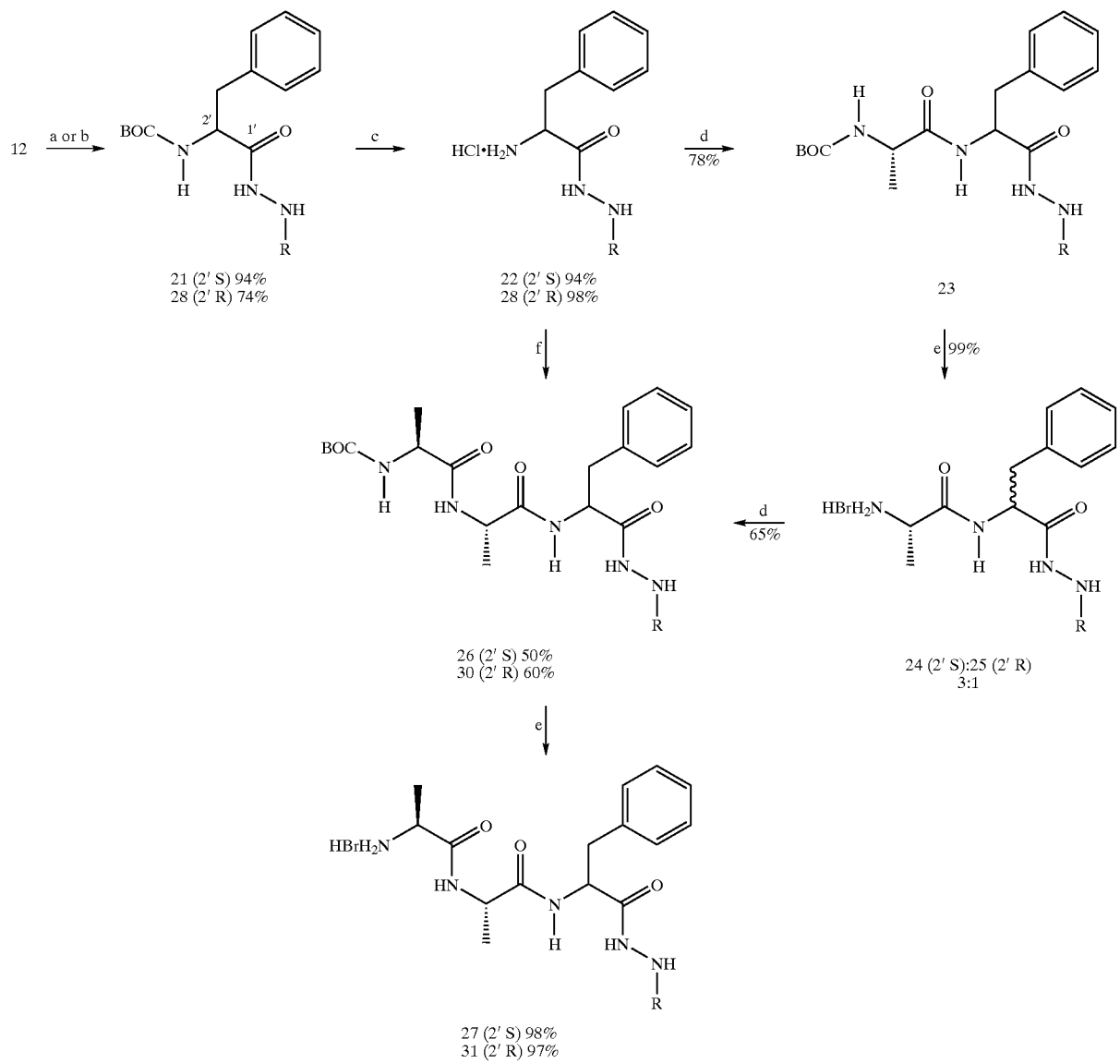

Scheme 5

R = anthraquinone
Reagents and conditions: (a) N-tBOC-L-Phe, EDC HCl, HOBt, NMM, THF; (b) N-tBOC-D-Phe, EDC HCl, HOBt, NMM, THF; (c) 6N-HCl/dioxane; (d) N-tBOC-Ala, EDC HCl, HOBt, NMM, THF; (e) 30% HBr/AcOH (f) N-tBOC-Ala-Ala, EDC•HCl, HOBt, NMM, THF THF and diethyl ether were freshly distilled from sodium/benzophenone, and pyridine was freshly distilled from calcium hydride. All reactions in nonaqueous solvents were conducted in oven-dried or flame-dried glassware, under a positive pressure of argon, with magnetic stirring. Flash column chromatography was carried out on ICN silica gel with 40 µm average particle diameter. NMR spectra were recorded on either a Brucker AC-300 or a DPX-300 instrument ($^1H$ at 300 MHz and $^{13}C$ at 75 MHz) or on a Brucker DPX-400 MHz instrument ($^1H$ at 400 MHz and $^{13}C$ at 100 MHz). Spectra were obtained in $CDCl_3$ solution unless ions are reported here). High-resolution mass spectra were obtained at the University of Iowa Mass Spectrometry Facility. Elemental analyses were performed by Atlantic Microlab Inc. (Norcross, Ga.). All reagents not otherwise described were obtained from commercial sources and used without further purification.

General Procedure for Preparation of Hydrazinoanthraquinones 1 and 12. To a stirred solution of the anthraquinone (4 or 11, 19.8 mmol) in pyridine (90 mL) was added hydrazine monohydrate (59.9 mmol) dropwise, and the reaction mixture was heated at reflux for 1–3 hours. After the reaction mixture had cooled to room temperature, it was concentrated in vacuo. To obtain compound 12, this residue was purified by column chromatography ($CHCl_3$). Compound 1 was purified by crystallization from xylene followed by column chromatography ($CHCl_3$).

General Procedure for Peptide Bond Formation with EDC.HCl. A solution of 1-hydroxybenzotriazole (365 mg, 2.7 mmol), an N-tBOC-protected amino acid (2.7 mmol), and EDC.HCl (537 mg, 2.8 mmol) in THF (11 mL) was cooled in an ice bath and stirred for 10 min. To this reaction mixture, hydrazinoanthraquinone (643 mg, 2.7 mmol) and N-methylmorpholine (NMM, 273 mg, 2.7 mmol) were added, and the resulting mixture was stirred for 1 hour at 0° C. After removal of the ice bath, the reaction mixture was allowed to stand at room temperature for 14–19 hours, then washed with water and extracted with chloroform. After the combined organic layers were dried ($MgSO_4$ or $Na_2SO_4$), concentration in vacuo, and purification of the residue by flash column chromatography ($CHCl_3$ or $CHCl_3$:EtOAc:MeOH 47:50:3) gave the desired product.

General Procedure for Removal of N-tBOC Groups. (Bodanszky et al., 1984).

Hydrochloric Acid in Dioxane. The N-tBOC-aminoanthraquinonylhydrazide (1.2 mmol) was placed into a round bottom flask and 6 N HCl in dioxane (5 mL) was added. The suspension was stirred for 1 hour at room temperature. After removal of solvent by evaporation, the residue was crystallized from ethanol/ether.

Hydrobromic Acid in Acetic Acid. The N-tBOC-tripeptidyl-anthraquinonylhydrazide (1.18 mmol) was dissolved in a 30% solution of HBr in acetic acid (3 mL) and stirred for 1 hour at room temperature. After the reaction mixture was diluted with ether, the precipitate was collected by filtration, washed with ether, and purified by column chromatography ($CHCl_3$:EtOAc:MeOH, 45:50:5) or crystallization from ethanol/ether.

5-Chloro-1-anthraquinonylhydrazine (1). purple solid; $^1$H NMR δ 8.25 (dd, J=7.7, 1.3 Hz, 1H), 7.99 (dd, J=8.5, 1.3 Hz, 1H), 7.70–7.55 (m, 4H); $^{13}$C NMR δ 183.8, 182.5, 150.1, 148.4, 137.4, 136.9, 135.3, 135.1, 134.9, 133.5, 129.5, 126.5, 119.5, 118.3; EIMS, m/z (relative intensity) 274 ([M+2]$^+$, 3), 272 (M$^+$, 8), 257 (10), 242 (8), 229 (20), 187 (4), 173 (8), 159 (17), 145 (11), 132 (100), 119 (41), 105 (24), 95 (41), 81 (17), 69 (16), 55 (17).

N-tBOC-Ala-5-chloro-1-anthraquinonylhydrazide (2). HOBt (28 mg, 0.21 mmol), EDC.HCl (42 mg, 0.22 mmol) and N-tBOC-L-Ala (40 mg, 0.21 mmol) were suspended in THF (0.9 mL) and stirred for 15 min at 0° C. 7-Chloropyrazoloanthrone (7.54 mg, 0.2 mmol) and N-methylmorpholine (23 μL) were added and the reaction mixture was stirred for 2 hours at 0° C. After removal of the ice bath, the reaction mixture was allowed to warm to room temperature and stirred for 14 hours. The reaction mixture was diluted with water and extracted with chloroform. The combined organic layers were washed with brine and dried over $MgSO_4$. Final purification by column chromatography (silica gel, 9:1, chloroform/EtOAc) gave compound 2 (48 mg, 0.11 mmol, 51%) as a dark red solid and compound 5/6 (2.2 mg, 5.2 μmol, 2%) as a dark red solid: $^1$H (DMSO) δ 10.35 (s, 1H, exchanges with $D_2O$), 10.28 (s, 1H, exchanges with $D_2O$), 8.25 (dd, J=7.59, 1.69 Hz, 1H), 7.92 (dd, J=8.1, 1.49 Hz, 1H), 7.87 (dd, J=7 Hz, 86, 7.75, 1H), 7.67 (t, J=8.11 Hz, 1H), 7.53 (d, J=6.44 Hz, 1H), 7.36 (d, J=8.53 Hz, 1H), 7.20 (d, J=6.61 Hz, 1H, exchanges with $D_2O$), 4.12–4.02 (m, 1H), 1.42 (s, 9H), 1.29 (d, J=7.23 Hz, 3H); $^{13}$C NMR (DMSO) δ 183.2, 181.4, 172.6, 155.4, 151.4, 136.9, 136.9, 136.7, 135.7, 135.0, 134.5, 133.1, 128.7, 126.4, 118.1, 117.4, 112.5, 79.2, 48.8, 28.2 (3C), 17.4; HRMS (FAB) calcd for $C_{22}H_{23}N_3O_5Cl$ (M+H)$^+$ 444.1326, found 444.1315.

N-tBOC-Ala-5-chloro-1-anthra[1,9-cd]pyrozol-6(2H)-one (5 or isomer 6). A solution of 1-hydroxybenzotriazole (50 mg, 0.37 mmol), N-tBOC-L-Ala (69 mg, 0.37 mmol), and EDC.HCl (74 mg, 0.37 mmol) in THF (1.7 mL) was cooled in an ice bath and stirred for 10 minutes. To this reaction mixture, compound 1 (100 mg, 0.37 mmol) and N-methylmorpholine (0.04 mL, 0.37 mmol) were added and the resulting mixture was stirred for 1 hour at 0° C. After removal of the ice bath, the reaction mixture was allowed to stand at room temperature for 14 hours, then washed with water and extracted with chloroform. After the combined organic layers were dried ($MgSO_4$ or $Na_2SO_4$), concentration in vacuo, and purification of the residue by flash column chromatography ($CHCl_3$) gave compound 5/6 as a dark red solid (101 mg, 65%): $^1$H δ 8.39 (d, J=8.1 Hz, 1H), 8.24 (dd, J=6.6, 2.2 Hz, 1H), 8.04 (d, J=7.3 Hz, 1H), 7.77 (t, J=7.8 Hz, 1H), 7.64–7.57 (m, 2H), 5.76–5.66 (m, 1H), 5.44 (d, J=8.1 Hz, 1H), 1.65 (d, J=6.9 Hz, 3H), 1.49 (s, 9H); $^{13}$C NMR δ181.1, 173.6, 155.1, 144.1, 137.9, 137.3, 135.0, 133.2, 132.2, 131.6, 129.6, 126.4, 124.6, 123.6, 123.1, 120.7, 80.1, 49.2, 28.2 (3C), 19.2; HRMS (FAB) calcd for $C_{22}H_{21}N_3O_4Cl$ (M+H)$^+$ 426.1221, found 426.1226.

7-Chloropyrazoloanthrone (7). To a stirred suspension of 1,5-dichloroanthraquinone (343 mg, 1.2 mmol) and iPr$_2$NEt (240 mg, 1.9 mmol) in THF (5.5 mL) was added hydrazine monohydrate (186 mg, 3.7 mmol) dropwise, and the reaction mixture was heated at reflux for 2 hours. After cooling, the mixture was washed with water and extracted with chloroform. The combined organic layers were washed with brine and dried over $MgSO_4$. Then the residue was separated by column chromatography (silica gel) with chloroform/EtOAc (1/1) as an eluent to give 7-chloropyrazoloanthrone (7) as a brown solid (57 mg, 18%); $^1$H NMR (DMSO) δ 8.23 (dd, J=7.11, 1.86 Hz, 1H), 7.88–7.82 (m, 2H), 7.78–7.62 (m, 2H), 7.34 (dd, J=7.25, 0.69 Hz, 1H); $^{13}$C NMR (DMSO) δ 181.7, 153.7, 137.1, 136.3, 135.5, 134.7, 134.3, 133.0 (2C), 128.6, 126.2, 118.2, 115.2, 110.0.

Ala-5-chloro-1-anthra[1,9-cd]pyrozol-6(2H)-one (8). red solid; $^1$H NMR (CD$_3$OD) δ 8.24 (d, J=8.1 Hz, 1H), 8.04 (dd, J=3.2, 6.0 Hz, 1H), 7.82 (d, J=7.4 Hz, 1H), 7.70 (t, J=8.0 Hz, 1H), 7.55–7.49 (m, 2H) 5.21 (q, J=7.1 Hz, 1H), 1.80 (d, J=7.1 Hz, 3H); $^{13}$C NMR(CD$_3$OD)δ 181.9, 170.9, 146.3, 139.1, 138.2, 136.7, 134.9, 133.5, 132.9, 130.7, 127.7, 125.8, 124.8, 124.4, 121.4, 50.7, 17.3, HRMS (FAB) calcd for $C_{17}H_{13}N_3O_2Cl$ (M−Cl)$^+$ 326.0696, found 326.0721.

N-tBOC-Gly-L-Pro-L-Ala-5-chloro-1-anthra[1,9-cd]pyrazol-6(2H)-one (9). yellow solid; $^1$H NMR δ 8.42 (d, J=8.1 Hz, 1H), 8.28 (dd, J=7.1, 1.8 Hz, 1H), 8.08 (d, J=7.3 Hz, 1H), 7.80 (t, J=7.8 Hz, 1H), 7.67–7.59 (m, 2H), 5.87–5.82 (m, 1H), 5.52 (s, 1H), 4.70 (dd, J=6.1, 1.6 Hz, 1H), 4.01 (dd, J=5.0, 5.0 Hz, 2H), 3.64–3.57 (m, 1H), 3.50–3.41 (m, 1H), 2.42–1.91 (m, 4H), 1.67 (d, J=7.0 Hz, 3H), 1.47 (s, 9H); $^{13}$C NMR δ 181.3, 172.7, 170.6, 168.7, 155.8, 144.3, 138.0, 137.4, 135.1, 133.2, 132.3, 131.7, 129.8, 126.5, 124.7, 123.8, 123.2, 120.8, 79.8, 60.6, 48.5, 46.4, 43.1, 28.3 (3C), 27.6, 24.9, 18.5; HRMS (FAB) calcd for $C_{29}H_{31}N_5O_6Cl$ (M+H)$^+$ 580.1963, found 580.1949.

Gly-L-Pro-L-Ala-5-chloro-1-anthra[1,9-cd]pyrozol-6 (2H)-one (10). yellow solid; $^1$H NMR (CD$_3$OD) δ 8.28 (d, J=7.9 Hz, 1H), 8.19 (dd, J=5.4, 1.6 Hz, 1H), 7.92 (d, J=7.4 Hz, 1H), 7.74 (t, J=7.6 Hz, 1H), 7.63–7.59 (m, 2H) 5.63 (q, J=6.9 Hz, 1H), 4.51 (dd, J=8.2, 3.7 Hz, 1H), 3.78 (s, 2H), 3.51–3.45 (m, 2H), 2.26–1.88 (m, 4H), 1.59 (d, J=7.3 Hz, 3H); $^{13}$C NMR ((CD$_3$)$_2$SO) δ 180.7, 172.7, 171.4, 164.3, 143.3, 137.6, 136.0, 135.1, 134.3, 132.3, 132.0, 129.3, 126.2, 124.1, 123.4, 123.2, 120.5, 59.0, 47.8, 47.7, 45.9, 29.4, 24.1, 16.8; HRMS (FAB) calcd for $C_{24}H_{23}N_5O_4Cl$ (M−Cl)$^+$ 480.1439, found 480.14.

1-Hydrazinoanthraquinone (12). (Moehlau et at., 1912; Xu et al., 1998). dark brown solid; $^1$H NMR δ 10.41 (s, 1H, exchanges with D$_2$O), 8.26–8.22 (m, 2H), 7.82–7.67 (m, 3H), 7.63–7.54 (m, 2H); $^{13}$C NMR δ 184.9, 183.7, 154.3, 135.2, 134.7, 134.2, 133.9, 133.0, 133.0, 126.8 (2), 118.3 (2), 116.5.

N-tBOC-Ala-1-anthraquinonylhydrazide (13). dark red solid; $^1$H NMR δ 10.48 (s, 1H, exchanges with D$_2$O), 8.77 (s, 1H, exchanges with D$_2$O), 8.12–8.08 (m, 2H), 7.66–7.58 (m, 3H), 7.43 (t, J=8.2 Hz, 1H), 7.17 (d, J=8.4 Hz, 1H), 5.37 (d, J=7.6 Hz, 1H), 4.22–4.38 (m, 1H), 1.49 (s, 9H), 1.46 (d, J=7.2 Hz, 3H); $^{13}$C NMR δ 185.1, 182.7, 172.7, 155.9, 150.9, 135.0, 134.1, 133.9, 133.7, 133.2, 132.5, 126.7, 126.5, 118.3, 117.6, 114.2, 80.5, 48.6, 28.3 (3C), 17.7; HRMS (FAB) calcd for $C_{22}H_{24}N_3O_5$ (M+H)$^+$ 410.1716, found 410.1731. Anal. Calcd for $C_{22}H_{23}O_5N_3$: C, 64.52; H, 5.67; N, 10.27. Found: C, 64.45; H, 5.71; N, 10.21.

Ala-1-anthraquinonylhydrazide (14). red solid; $^1$H NMR (CD$_3$OD) δ 8.25 (dd, J=6.8, 2.0 Hz, 1H), 8.17 (dd, J=7.4, 1.7 Hz, 1H), 7.87–7.65 (m, 4H), 7.36 (dd, J=7.4, 1.2 Hz, 1H), 4.24–4.17 (m, 1H), 1.69 (d, J=6.9 Hz, 3H); $^{13}$C NMR (CD$_3$OD) δ 186.7, 184.4, 171.2, 152.6, 136.7, 135.8, 135.7, 135.5, 135.0, 134.2, 128.1, 127.8, 119.5, 119.3, 115.9, 64.4, 17.6; HRMS (FAB) calcd for $C_{17}H_{16}N_3O_3$ (M−Cl)$^+$ 310.1192, found 310.1206.

N-tBOC-Gly-L-Pro-L-Ala-1-anthraquinonylhydrazide (15). dark red solid; $^1$H NMR δ 10.51 (s, 1H, exchanges with D$_2$O), 9.06 (s, 1H, exchanges with D$_2$O), 8.23–8.17 (m, 2H), 7.75–7.66 (m, 3H), 7.55 (t, J=8.0 Hz, 1H), 7.26 (d, J=8.7 Hz, 1H), 7.20 (d, J=7.3 Hz, 1H, exchanges with D$_2$O), 5.45 (s, 1H), 4.65–4.52 (m, 2H), 4.02 (dd, J=16.6, 4.7 Hz, 1H), 3.78–3.71 (m, 2H), 3.55–3.47 (m, 1H), 2.22–1.98 (m, 4H), 1.50 (d, J=7.3 Hz, 3H), 1.46 (s, 9H); $^{13}$C NMR δ185.3, 183.3, 171.7, 171.6, 169.8, 156.4, 151.6, 135.4, 134.4, 134.2, 133.9 (2C), 133.3, 132.8, 127.0, 126.7, 118.5, 118.4, 80.5, 61.2, 48.5, 47.1, 43.4, 28.8, 28.3 (3C), 24.9, 16.9; HRMS (FAB) calcd for $C_{29}H_{13}N_5O_7Na$ (M+Na)$^+$ 586.2278, found 586.2277.

Gly-L-Pro-L-Ala-1-anthraquinonylhydrazide (16). dark red solid; $^1$H NMR (CD$_3$OD) δ 8.31 (dd, J=7.5, 1.5 Hz, 1H), 8.34 (dd, J=7.0, 1.8 Hz, 1H), 7.90–7.80 (m, 2H), 7.75–7.64 (m, 2H), 7.43 (d, J=8.1 Hz, 1H), 4.53–4.44 (m, 2H), 3.78–3.53 (m, 4H), 2.39–1.95 (m, 4H), 1.54 (d, J=7.1 Hz, 3H); $^{13}$C NMR (CD$_3$OD) δ 186.7, 184.6, 175.1, 175.1, 174.8, 153.1, 136.6, 135.8, 135.7, 135.6, 135.0, 134.3, 128.1, 127.8, 119.9, 119.3, 115.7, 67.1, 61.9, 60.0, 47.9, 30.9, 25.8, 17.6; HRMS (FAB) calcd for $C_{24}H_{26}N_5O_5$ (M−Br)$^+$ 464.1934, found 464.1950.

N-tBOC-O-Benzyl-L-Ser-1-anthraquinonylhydrazide (17). dark red solid; $^1$H NMR δ 10.54 (s, 1H, exchanges with D$_2$O), 8.31–8.21 (m, 3H), 7.78–7.71 (m, 3H), 7.42–7.30 (m, 5H), 7.23 (d, J=8.5 Hz, 1H), 5.46 (d, J=6.7 Hz, 1H), 4.64 (d, J=11.7 Hz, 1H), 4.59 (d, J=11.7 Hz, 1H), 4.51 4.48 (m, 1H), 4.00 (dd, J=8.8, 3.6 Hz, 1H), 3.70 (dd, J=9.0, 6.4 Hz, 1H), 1.49 (s, 9H); $^{13}$C NMR δ 185.3, 182.9, 170.4, 155.5, 151.0, 137.1, 135.1, 134.1, 134.0, 133.8, 133.3, 132.6, 128.5 (2C), 128.0, 127.9 (2C), 126.8, 126.6, 118.4, 118.0, 114.4, 80.7, 73.7, 69.7, 53.4, 28.3 (3C); HRMS (FAB) calcd for $C_{29}H_{30}N_3O_6$ (M+H)$^+$ 516.2135, found 516.2129.

O-Benzyl-L-Ser-1-anthraquinonylhydrazide (18). red solid; $^1$H NMR (CD$_3$OD) δ 8.18 (dd, J=8.9, 3.3 Hz, 1H), 8.10 (dd, J=7.3, 1.8 Hz, 1H), 7.88–7.67 (m, 3H), 7.60 (dd, J=7.5, 1.1 Hz, 1H), 7.42–7.29 (m., 5H), 7.21 (dd, J=8.5, 1.3 Hz, 1H), 4.67 (d, J=11.9 Hz, 1H), 4.61 (d, J=11.9 Hz, 1H), 4.30 (t, J=4.4 Hz, 1H), 4.01–3.93 (m, 2H); $^{13}$C NMR (CD$_3$OD) δ 186.8, 184.4, 168.4, 152.5, 138.5, 136.6, 135.8, 135.7, 135.5, 135.0, 134.2, 129.8 (2C), 129.4 (3C), 128.1, 127.8, 119.5, 119.5, 115.9, 74.9, 69.1, 53.8; HRMS (FAB) calcd for $C_{24}H_{22}N_3O_4$ (M−Cl)$^+$ 416.1610, found 416.1607.

N-tBOC-Gly-L-Pro-O-benzyl-L-Ser-1-anthraquinonylhydrazide (19). dark red solid; $^1$H NMR δ 10.56 (s, exchanges with D$_2$O), 8.84 (s, exchanges with D$_2$O), 8.29–8.16 (m, 2H), 7.79–7.70 (m, 4H), 7.47–7.22 (m, 6H), 4.76–4.52 (m, 3H), 4.09 (dd, J=9.4, 3.6 Hz, 1H), 4.00–3.90 (m, 2H), 3.72 (dd, J=10.0, 4.9 Hz, 1H), 3.69–3.61 (m, 1H), 3.53–3.48 (m, 2H), 2.25–2.01 (m, 4H), 1.43 (s, 9H); $^{13}$C NMR δ 186.8, 183.3, 171.1, 169.6, 169.2, 156.8, 151.4, 137.3, 135.4, 134.4, 134.3, 133.9, 133.4, 132.9, 128.6 (2C), 128.1, 127.7 (2C), 127.0, 126.8, 118.5, 118.3, 114.6, 80.1, 73.5, 68.9, 61.2, 52.8, 46.8, 43.2, 28.5, 28.2 (3C), 24.9; HRMS (FAB) calcd for $C_{36}H_{39}N_5O_8Na$ (M+Na)$^+$ 692.2696, found 692.2693.

Gly-L-Pro-L-Ser-1-anthraquinonylhydrazide (20). dark red solid; $^1$H NMR (CD$_3$OD) δ 8.32 (dd, J=8.9, 3.3 Hz, 1H), 8.24 (dd, J=7.3, 1.8 Hz, 1H), 7.88–7.81 (m, 2H), 7.76–768 (m, 2H), 7.53 (dd, J=7.5, 1.1 Hz, 1H), 4.61–4.53 (m, 2H), 3.69–3.54 (m, 4H), 2.37–2.32 (m, 2H, 2.14–2.06 (m, 2H); $^{13}$C NMR (CD$_3$OD) δ 186.8, 184.6, 167.7, 166.8, 166.4, 153.2, 136.6, 135.8, 135.8, 135.6, 135.0, 134.3, 128.1, 127.8, 120.1, 119.3, 113.4, 62.1, 60.7, 47.5, 41.6, 30.3, 26.1, 20.9; HRMS (FAB) calcd for $C_{24}H_{27}N_5O_6$ (M−Br+H)$^+$ 481.1961, found 481.1961.

N-tBOC-L-Phe-1-anthraquinonylhydrazide (21) and N-tBOC-D-Phe-1-anthraquinonylhydrazide (28). golden orange solid; $^1$H NMR δ 10.47 (s, 1H), 8.27–8.21 (m, 2H), 7.76–7.70 (m, 3H), 7.45–7.21 (m, 6H), 6.78 (d, J=8.25 Hz, 1H), 5.16 (br, 1H), 4.53–4.44 (m, 1H), 3.14 (d, J=7.31 Hz, 2H), 1.48 (s, 9H); $^{13}$C NMR δ 185.6, 183.2, 171.0, 151.1, 136.2, 135.3, 134.4, 134.3, 134.0, 133.5, 132.9, 129.4 (3C), 129.0 (2C), 127.2, 127.0, 126.9, 118.7, 118.0, 114.6 81.9, 54.6, 37.8, 28.3 (3C); 21, HRMS (FAB) calcd for $C_{28}H_{28}N_3O_5$ (M+H)$^+$ 486.2029, found 486.2036; 28, HRMS (FAB) calcd for $C_{28}H_{28}N_3O_5$ (M+H)$^+$ 486.2029, found 486.2032.

L-Phe-1-anthraquinonylhydrazide (22) and D-Phe-1-anthraquinonylhydrazide (29). dark orange solid; $^1$H NMR (CD$_3$OD) δ 8.23 (dd, J=7.2, 1.3 Hz, 1H), 8.15 (dd, J=7.2, 1.9 Hz, 1H), 7.92–7.74 (m, 2H), 7.63 (dd, J=7.4, 1.0 Hz, 1H), 7.45–7.31 (m, 6H), 6.53 (dd, J=8.5, 1.0 Hz, 1H), ?3.98 (t, J=7.2 Hz, 1H), 3.13 (d, J=1.5 Hz, 1H), 3.11 (d, J=2.9 Hz, 1H); $^{13}$C NMR δ 186.7, 184.5, 173.7, 152.4, 137.6, 136.6, 135.8, 135.6, 135.5, 134.9, 134.3, 130.8 (2C), 130.2 (2C), 128.7, 128.1, 127.7, 119.6, 119.2, 115.6, 56.0, 41.1; 22, HRMS (FAB) calcd for C$_{23}$H$_{20}$N$_3$O$_3$ (M+H)$^+$ 386.1505, found 386.1509; 29 HRMS (FAB) calcd for C$_{23}$H$_{20}$N$_3$O$_3$ (M+H)$^+$ 386.1505, found 386.1504.

N-tBOC-L-Ala-L-Phe-1-anthraquinonylhydrazide (23). dark orange solid; $^1$H NMR δ 10.40 (s, 1H), 8.13 (dd, J=5.3, 5.3 Hz, 2H), 7.76–7.57 (m, 4H), 7.32–7.29 (m, 6H), 6.49 (d, J=6.6 Hz, 1H), 5.71 (d, J=7.6 Hz, 1H), 4.89–4.87 (m, 1H), 4.19–4.14 (m, 1H), 3.18 (br, 2H), 1.42 (s, 9H), 1.24 (d, J=16.4 Hz, 3H); $^{13}$C NMR δ 185.1, 183.1, 173.5, 170.8, 155.7, 150.8, 150.6, 136.0, 135.0, 134.0, 133.8, 133.2, 132.5, 129.3 (2C), 128.3 (2C), 127.0, 126.7, 126.6, 118.2, 117.9, 113.9, 80.3, 52.7, 50.1, 37.7, 28.1 (3C), 17.7; HRMS calcd for C$_{31}$H$_{33}$N$_4$O$_6$ (M+H)$^+$ 557.2400, found 557.2404.

L-Ala-L-Phe-1-anthraquinonylhydrazide (24). dark orange solid; $^1$H NMR (CD$_3$OD) δ 8.26–8.15 (m, 2H), 7.86–7.62 (m, 3H), 7.52–7.36 (m, 6H), 6.59 (d, J=8.5 Hz, 1H), 4.39–4.33 (m, 1H), 4.24–4.21 (m, 1H), 3.29 (d, J=8.0 Hz, 2H), 1.56 (dd, J=10.0, 7.3 Hz, 3H); $^{13}$C NMR (CD$_3$OD) δ 186.7, 184.4, 173.1, 169.8, 152.6, 152.6, 137.8, 136.7, 135.6, 135.5, 134.9, 134.2, 130.9 (2C), 130.4 (2C), 128.4, 128.1, 127.8, 119.5, 119.3, 115.7, 55.4, 54.7, 38.6, 17.8; HRMS (FAB) calcd for C$_{26}$H$_{25}$N$_4$O$_4$ (M+) 457.1876, found 457.1887.

N-tBOC-L-Ala-L-Ala-L-Phe-1-anthraquinonylhydrazide (26). orange solid; $^1$H NMR δ 8.47 (d, J=7.4 Hz, 1H), 8.45 (d, J=8.0 Hz, 1H), 8.33 (d, J=7.8 Hz, 1H), 8.17 (d, J=7.4 Hz, 1H), 7.85–7.79 (m, 2H), 7.75–7.67 (m, 2H), 7.29–7.10 (m, 5H), 6.72–6.94 (m, 1H), 6.24–6.18 (m, 1H), 4.97–4.94 (m, 1H), 4.55–4.50 (m, 1H), 4.144.04 (m, 1H), 3.49 (dd, J=14.2, 5.5 Hz, 1H), 3.29 (dd, J=13.6, 7.2 Hz, 1H), 1.46 (s, 9H), 1.38 (d, J=6.9 Hz, 3H), 1.34 (d, J=7.2 Hz, 3H); $^{13}$C NMR δ 184.4, 182.6, 172.5, 171.6, 171.2, 155.0, 144.6, 138.2, 135.6, 134.2, 133.6, 131.5, 131.0, 129.4, 129.3, 129.2 (2C), 128.5 (2C), 127.0, 124.2, 123.8, 121.0, 115.7, 80.5, 53.4, 48.9, 48.9, 38.7, 28.3 (3C), 18.0, 17.9; HRMS calcd for C$_{34}$H$_{38}$N$_5$O$_7$ (M+H)$^+$ 628.2771, found 628.2774.

L-Ala-L-Ala-L-Phe-1-anthraquinonylhydrazide (27). dark orange solid; $^1$H NMR (CD$_3$OD) δ 8.31 (dd, J=6.7, 1.7 Hz, 1H), 8.23 (d, J=7.0, 1.3 Hz, 1H), 7.88 (dt, J=7.4, 1.7 Hz, 2H), 7.70 (dd, J=7.5, 0.9 Hz, 1H), 7.52 (dd, J=8.4, 7.7 Hz, 1H), 7.40–7.22 (m, 5H), 6.78 (dd, J=8.6, 0.8 Hz, 1H), 4.72 (t, J=8.0 Hz, 1H), 4.39 (dd, J=7.1, 2.6 Hz, 1H), 3.58 (dd, J=7.4, 7.4 Hz, 1H), 3.18 (d, J=12.7 Hz, 2H), 1.51 (d, J=7.1 Hz, 3H), 1.39 (d, J=7.2 Hz, 3H); $^{13}$C NMR (CD$_3$OD) δ 186.7, 184.5, 174.7, 173.3, 170.9, 152.7, 138.0, 136.6, 135.8, 135.6, 135.5, 135.0, 134.3, 130.7 (2C), 130.0 (2C), 128.3, 128.1, 127.8, 119.8, 119.2, 115.4, 55.5, 54.4, 55.2, 38.8, 18.3, 17.8; HRMS (FAB) calcd for C$_{29}$H$_{30}$N$_5$O$_5$ (M−Br)$^+$ 528.2247, found 528.2253.

N-tBOC-L-Ala-L-Ala-D-Phe-1-anthraquinonylhydrazide (30). red-orange solid; $^1$H NMR δ 8.44 (d, J=7.0 Hz, 1H), 8.39 (d, J=8.0 Hz, 1H), 8.29 (d, J=7.1 Hz, 1H), 8.13 (d, J=7.0 Hz, 1H), 7.81–7.75 (m, 2H), 7.71–7.60 (m, 2H), 7.32–7.16 (m, 5H), 6.75–6.72 (m, 1H), 6.19–6.16 (m, 1H), 5.07–5.04 (m, 1H), 4.61–4.55 (m, 1H), 4.18–4.13 (m, 1H), 3.50 (dd, J=13.3, 5.4 Hz, 1H), 3.24 (dd, J=10.1, 7.7 Hz, 1H), 1.44 (s, 9H), 1.36 (d, J=6.0 Hz, 3H), 1.30 (d, J=6.9 Hz, 3H); $^{13}$C NMR δ 184.2, 182.5, 172.6, 171.8, 171.3, 155.6, 145.0, 138.1, 135.9, 134.2, 133.6, 131.4, 130.9, 129.5, 129.3 (2C), 128.7, 128.5 (2C), 127.2, 124.1, 123.7, 120.9, 118.3, 80.4, 53.5, 50.9, 48.8, 38.6, 28.3 (3C), 18.3, 18.0.

L-Ala-L-Ala-D-Phe-1-anthraquinonylhydrazide (31). dark red solid; $^1$H NMR (400 MHz, CD$_3$OD) δ 8.31 (dd, J=7.7, 1.5 Hz, 1H), 8.23 (dd, J=7.0, 1.6 Hz, 1H), 7.86 (dd, J=7.4, 1.9 Hz, 1H), 7.84 (dd, J=7.5, 1.6 Hz, 1H), 7.71 (dd, J=7.2, 0.9 Hz, 1H), 7.58 (dd, J=8.7, 7.4 Hz, 1H), 7.39–7.20 (m, 5H), 6.99 (dd, J=8.3, 0.8 Hz, 1H), 4.71 (dd, J=9.2, 4.0 Hz, 1H), 4.37 (q, J=7.2 Hz, 1H), 3.53 (q, J=7.2 Hz, 1H), 3.21 (dd, J=13.6, 5.2 Hz, 1H), 2.98 (dd, J=14.0, 9.2 Hz, 1H), 1.29 (d, J=7.2 Hz, 3H), 1.18 (d, J=6.8 Hz, 3H); $^{13}$C NMR (CD$_3$OD) δ 186.7, 184.5, 174.6, 172.9, 170.7, 155.6, 138.6, 136.7, 135.5, 135.1 (2C), 135.0, 130.6 (2C), 129.6 (2C), 128.2, 128.1, 128.0, 119.8, 119.2, 118.0, 55.6, 55.2, 55.0, 39.4, 18.6, 17.8; HRMS (FAB) calcd for C$_{29}$H$_{30}$N$_5$O$_5$ (M−Br)$^+$ 528.2247, found 528.2242.

EXAMPLE 2

Biological Evaluation of Compounds

C57BL/6J mice (6 to 8 weeks old) were purchased from the Jackson Laboratory (Bar Harbor, Me.). The mice were sacrificed with an overdose of anesthetic and then transcardially perfused with 0.9% (w/v) saline solution, followed by 2% paraformaldehyde in 0.2 M phosphate buffer. The tissues were removed and post-fixed for 2 hours. After fixation, the tissues were cryoprotected by immersion in 25% sucrose and frozen in OCT compound (Sakura Finetek U.S.A., Inc, Torrance, Calif.). Sections (10 μm) were cut with a cryostat and mounted onto gelatin-coated slides.

Sections were embedded in 0.5% celloidin, followed by incubation in substrate solutions. The sections were incubated in substrate solutions containing 1 mM of the compound, 1 mg/mL of benzaldehyde (BA) or p-anisaldehyde (p-AA) or p-nitrobenzaldehyde (p-NBA) in 0.1 M acetate buffer (pH 4.5) at 37° C. for 4 hours. Slides were rinsed and cover-slipped before viewing on a Leica DM RBE microscope equipped with a Spot-RT Digital Camera and associated software. For all experiments, tissue staining was repeated on a minimum of 5 sections/animal per compound. A minimum of three individual animals was tested to confirm consistency of the results.

Five different compounds, compounds 10, 16, 20, 27, and 31, were tested histochemically on frozen sections of murine tissues. The substrates were systematically compared for sensitivity to TPP-1 activity using conditions to control the rate of crystalline formation and diffusion of product. The results are summarized in Table 1. Among the five substrates, compounds 10, 20, and 27 were readily hydrolyzed by endogenous TPP-1 in murine tissues, revealing lysosomal accumulation of precipitates. There was no evidence of hydrolysis of tripeptides 16 and 31 by TPP-1. For compounds 10, 20, and 27, the aldehydes p-NBA and p-AA were more effective than benzaldehyde itself with regard to precipitate density and color. The combination of tripeptide 20 and p-AA was most sensitive, resulting in purple precipitates in areas of high endogenous enzyme activity (e.g., kidney; FIG. 1). Thus, compounds 10, 20, and 27 specifically detected TPP-1, with low to no background activity.

This combination of reagents was used to assess TPP-1 expression in murine brain following viral-mediated gene transfer. Recombinant protein was readily detectable in areas of low endogenous activity, demonstrating the utility of histochemical evaluation of CNS therapies for TPP-1 deficiency (data not shown).

TABLE 1

Intensity and color of the final reaction product of TPP-1 histochemical staining.

| Tripeptide | p-Anisaldehyde | p-Nitrobenzaldehyde | Benzaldehyde |
|---|---|---|---|
| 10 | +++<br>Yellow-green<br>Autofluorescent | +++<br>Yellow-green<br>Autofluorescent | ++<br>Yellow-green<br>Autofluorescent |
| 16 | – | – | – |
| 20 | +++<br>Dark Purple | +++<br>Brown | +<br>Brown |
| 27 | +++<br>Yellow-green | +++<br>Yellow-green | ++<br>Yellow-green |
| 31 | – | – | – |

REFERENCES

Bennett et al., *J. Inherit. Metab. Dis.*, 22, 535–544 (1999).
Bodanszky, M.; Bodanszky, A. The Practice of Peptide Synthesis. Springer-Verlag, Berlin, N.Y., pages 145 and 165 (1984).
Bradley et al., *J. Chem. Soc.*, 1630–1635 (1952).
Dikov et al., *Cell. Mol. Biol.*, 46, 1219–1225 (2000).
Haskell et al., *Gene Therapy*, 10, 34–42 (2003).
Moehlau, *Chem. Ber.*, 45, 2233–2247 (1912).
Mole et al., *Neurobiol. Dis.*, 5, 287–303 (1998).
Page et al., *Arch. Biochem. Biophys.*, 306, 354–359 (1993).
Palmer et al, *Am. J. Med. Genet.*, 57, 260–265 (1995).
Sheehan et al., *J. Org. Chem.*, 26, 2525–2528 (1961).
Sleat et al., *Science*, 277, 1802–1805 (1997).
Vines et al, *Biochim. Biophys. Acta.*, 1384, 233–242 (1998).
Xu et al., *J. Org. Chem.*, 63, 4314–4322 (1998).
Zhang et al., *Tetrahedron Lett.*, 35, 3675–3678 (1994).

All publications, patents and patent applications referred to herein are incorporated by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:
1. A compound of formula I:

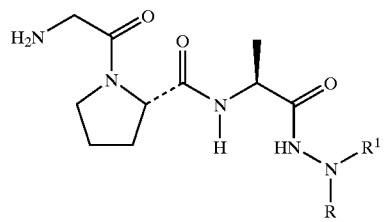

or a salt thereof, wherein
R is an anthraquinone, and
$R^1$ is
(a) H, or
(b) $C_{1-6}$alkyl.
2. The compound of claim 1, which is Gly-L-Pro-L-Ala-1-anthraquinonylhydrazide, or a salt thereof.
3. A compound of formula II:

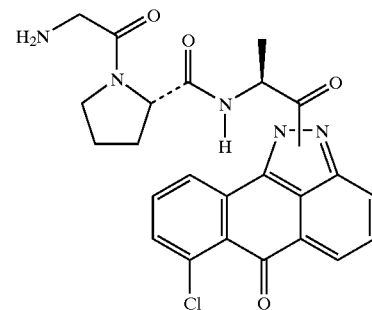

or a salt thereof.
4. The compound of claim 3, which is a bromide salt.
5. A compound of formula III:

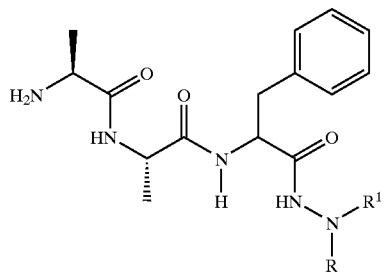

or a salt thereof, wherein
R is an anthraquinone, and
$R^1$ is
(a) H, or
(b) $C_{1-6}$alkyl.
6. The compound of claim 5, which is L-Ala-L-Ala-L-Phe-1-anthraquinonylhydrazide, or a salt thereof.
7. A composition, comprising the compound of claim 1, 3, or 5.
8. The composition of claim 7, further comprising p-anisaldehyde.
9. The composition of claim 7, further comprising p-nitrobenzaldehyde.

10. The composition of claim 7, further comprising benzaldehyde.

11. A method for detecting or determining tripeptidyl protease 1 (TPP-1) in a biological sample from a mammal, comprising contacting the sample with the composition of claim 7 and detecting or determining TPP-1 in the sample.

12. A kit, comprising the compound of claim 1, 3, or 5 and a first container, packaging material, and instructions for the use of the kit to detect or determine tripeptidyl protease 1 in a biological sample, wherein the compound of claim 1, 3, or 5 is disposed in said first container.

13. The kit of claim 12, further comprising p-anisaldehyde.

14. The kit of claim 13, further comprising a second container, wherein the p-anisaldehyde is disposed in said second container.

15. The kit of claim 12, further comprising p-nitrobenzaldehyde.

16. The kit of claim 15, further comprising a second container, wherein p-nitrobenzaldehyde is disposed in said second container.

17. The kit of claim 12, further comprising benzaldehyde.

18. The kit of claim 17, further comprising a second container, wherein benzaldehyde is disposed in said second container.

* * * * *